US012639806B2

(12) United States Patent
Inoue et al.

(10) Patent No.: US 12,639,806 B2
(45) Date of Patent: May 26, 2026

(54) MEDICAL SYSTEM, INFORMATION PROCESSING METHOD, AND COMPUTER-READABLE MEDIUM FOR CALCULATING PRESENCE PROBABILITY OF LESION IN NOT-YET-OBSERVED REGION

(71) Applicant: OLYMPUS CORPORATION, Tokyo (JP)

(72) Inventors: Nao Inoue, Tokyo (JP); Shuma Sasaki, Tokyo (JP); Mitsunori Kubo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 564 days.

(21) Appl. No.: 17/898,903

(22) Filed: Aug. 30, 2022

(65) Prior Publication Data

US 2022/0414880 A1     Dec. 29, 2022

Related U.S. Application Data

(63) Continuation of application No. PCT/JP2020/009494, filed on Mar. 5, 2020.

(51) Int. Cl.
*G06T 7/00*     (2017.01)
*A61B 1/00*     (2006.01)

(52) U.S. Cl.
CPC ........ *G06T 7/0012* (2013.01); *A61B 1/00009* (2013.01); *G06T 2207/10068* (2013.01)

(58) Field of Classification Search
CPC . G06T 2207/10068; G06T 2207/30028; G06T 2207/30032; G06T 2207/30092; G06T 2207/30096; G06T 7/0012; G06T 2200/24; G06T 2207/10016; A61B 1/00009; A61B 1/000094; A61B 1/000096; A61B 1/0005; A61B 1/0638

See application file for complete search history.

(56) References Cited

U.S. PATENT DOCUMENTS

| | | | |
|---|---|---|---|
| 9,547,940 B1 * | 1/2017 | Sun ........................ | G06T 7/344 |
| 2001/0031920 A1 * | 10/2001 | Kaufman ............... | A61B 5/055 |
| | | | 600/431 |
| 2009/0073257 A1 * | 3/2009 | Tanaka .................. | G06T 7/0012 |
| | | | 348/E13.001 |
| 2017/0046833 A1 * | 2/2017 | Lurie ..................... | G06T 17/20 |

(Continued)

FOREIGN PATENT DOCUMENTS

JP     2016-087370 A     5/2016

OTHER PUBLICATIONS

International Search Report dated Apr. 21, 2020 received in PCT/JP2020/009494.

*Primary Examiner* — Stephen S Hong
*Assistant Examiner* — Carl E Barnes, Jr.
(74) *Attorney, Agent, or Firm* — Scully, Scott, Murphy & Presser, P.C.

(57) ABSTRACT

A medical system includes a processor. The processor is configured to calculate a presence probability of a lesion in a not-yet-observed region inside a hollow organ of a patient, the not-yet-observed region being specified on the basis of an image that has been captured by an imaging sensor of an endoscope inside the hollow organ, and spatial disposition information of a distal end of an insertion part of the endoscope.

19 Claims, 9 Drawing Sheets

(56)                 References Cited

U.S. PATENT DOCUMENTS

| | | | |
|---|---|---|---|
| 2017/0084027 A1* | 3/2017 | Mintz | A61B 1/2676 |
| 2018/0253839 A1* | 9/2018 | Zur | A61B 1/000094 |
| 2019/0380617 A1* | 12/2019 | Oosake | A61B 1/00006 |
| 2020/0279368 A1* | 9/2020 | Tada | A61B 1/00016 |
| 2020/0337537 A1* | 10/2020 | Hirasawa | A61B 1/000096 |
| 2021/0068750 A1* | 3/2021 | Stone | A61B 5/4887 |
| 2021/0153808 A1* | 5/2021 | Tada | G06T 7/0016 |

* cited by examiner

T1

| PRESENCE PROBABILITY | RECOMMENDED EXAMINATION DATE |
|---|---|
| 0–5% | WITHIN X YEARS |
| 5–30% | WITHIN Y MONTHS |
| 30–70% | WITHIN Z MONTHS |

| MALIGNANCY GRADE | RECOMMENDED EXAMINATION DATE |
|---|---|
| A IS PRESENT | WITHIN Z MONTHS |
| B IS PRESENT (X PIECES OR MORE) | WITHIN Y MONTHS |
| B IS PRESENT (LESS THAN X PIECES), AND C IS PRESENT | WITHIN X YEARS |

FIG. 12

MEDICAL SYSTEM, INFORMATION PROCESSING METHOD, AND COMPUTER-READABLE MEDIUM FOR CALCULATING PRESENCE PROBABILITY OF LESION IN NOT-YET-OBSERVED REGION

CROSS REFERENCE TO RELATED APPLICATIONS

This is a Continuation Application of PCT Application No. PCT/JP2020/009494, filed Mar. 5, 2020, which was not published under PCT Article 21(2) in English.

TECHNICAL FIELD

The disclosure herein relates to a medical system, an information processing method, and a computer-readable medium.

BACKGROUND

Endoscopy is an examination method for inserting an endoscope into a hollow organ such as the esophagus, stomach, large intestine, trachea, or bronchus, and observing the inside of the lumen by using an image obtained by the endoscope. The usefulness of endoscopy is currently recognized widely. For example, by conducting large intestine magnifying endoscopy by using the technology described in JP 2016-087370 A, a colorectal polyp can be classified as a tumor or a non-tumor on the basis of a surface structure of the colorectal polyp, and in the case of the tumor, the tumor can be classified as a benign tumor or a malignant tumor. As described above, endoscopy enables the inside of the lumen to be directly observed, and therefore a lesion can be detected early, and can be treated early.

SUMMARY

A medical system in an aspect of the present embodiment includes a processor, and the processor is configured to calculate a presence probability of a lesion in a not-yet-observed region inside a hollow organ of a patient, the not-yet-observed region being specified on the basis of an image that has been captured by an imaging sensor of an endoscope inside the hollow organ, and spatial disposition information of a distal end of an insertion part of the endoscope.

In an information processing method in an aspect of the present embodiment, a computer calculates a presence probability of a lesion in a not-yet-observed region inside a hollow organ of a patient, the not-yet-observed region being specified on the basis of an image that has been captured by an imaging sensor of an endoscope inside the hollow organ, and spatial disposition information of a distal end of an insertion part of the endoscope.

A non-transitory computer-readable medium in an aspect of the present embodiment stores a program that causes a computer to perform a process including calculating a presence probability of a lesion in a not-yet-observed region inside a hollow organ of a patient, the not-yet-observed region being specified on the basis of an image that has been captured by an imaging sensor of an endoscope inside the hollow organ, and spatial disposition information of a distal end of an insertion part of the endoscope.

BRIEF DESCRIPTION OF DRAWINGS

The present embodiment will be more apparent from the following detailed description when the accompanying drawings are referenced.

FIG. 11 is a diagram for explaining an example of a method for determining recommended examination date.

FIG. 12 is a diagram for explaining another example of the method for determining recommended examination date.

DESCRIPTION OF EMBODIMENTS

It is requested that endoscopy be finished in as short a time as possible in order to reduce distress of a patient, and it is not always easy to thoroughly observe the inside of a hollow organ under the restrictions described above. Embodiments are described below.

Figure 1:
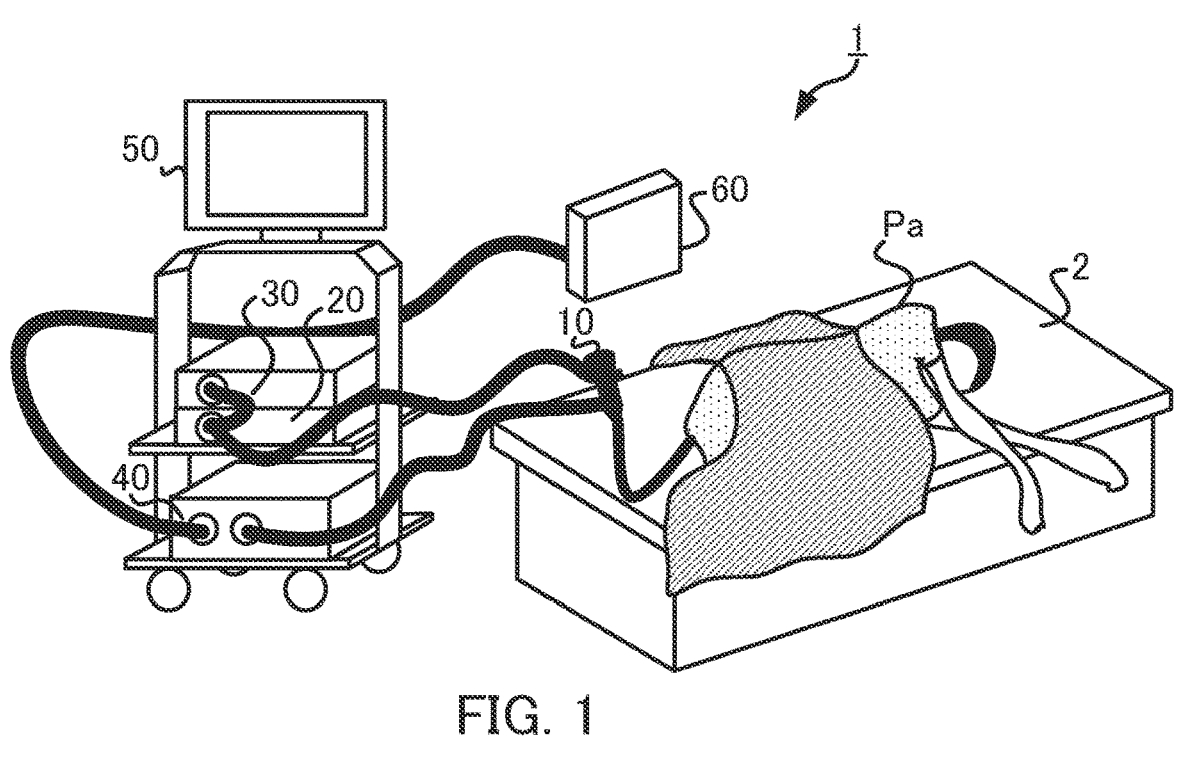
FIG. 1 is a diagram illustrating a configuration of a medical system according to an embodiment.
Figure 2:
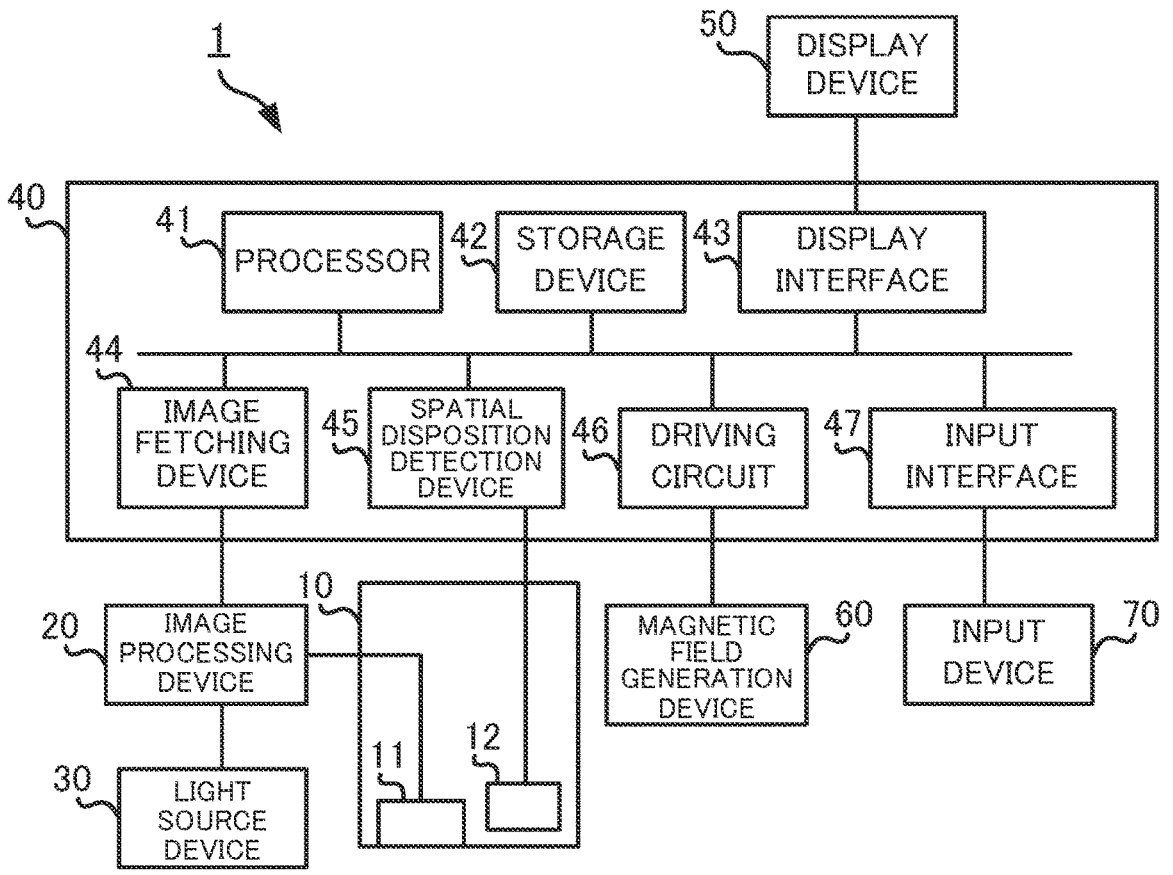
FIG. 2 is a block diagram illustrating a configuration of a medical system according to an embodiment.

FIG. 1 is a diagram illustrating a configuration of a medical system according to an embodiment. FIG. 2 is a block diagram illustrating a configuration of a medical system according to an embodiment. A medical system 1 illustrated in FIGS. 1 and 2 is a system that generates a next examination plan on the basis of a result of endoscopy conducted on a hollow organ of a patient Pa. In addition, the medical system 1 is a system that processes, in real time, information obtained during endoscopy to provide a doctor with a live image and auxiliary information that helps improvements in the precision and efficiency of examination. A configuration of the medical system 1 is described below with reference to FIGS. 1 and 2.

The medical system 1 includes an endoscope 10, an image processing device 20, a light source device 30, an examination assistance device 40, a display device 50, a magnetic field generation device 60, and an input device 70, as illustrated in FIG. 1. Note that the endoscope 10 is not particularly limited, but is, for example, a flexible endoscope for the large intestine. The description below is provided by using, as an example, a case where colonoscopy is conducted by using a flexible endoscope, but a range of application of the medical system 1 is not limited to colonoscopy. The medical system 1 can also be applied to endoscopy of another hollow organ such as the esophagus or stomach. In addition, it is sufficient if an endoscopic image that has been obtained while moving inside the lumen and its coordinate information are obtained. Therefore, in endoscopy, a flexible endoscope does not always need to be used, and a rigid endoscope may be used.

The endoscope 10 includes an operation part that is operated by a doctor, an insertion part that is inserted into the lumen and has flexibility, a universal cord that extends from the operation part, and a connector part that is provided at an end of the universal cord and is detachably connected to the image processing device 20 and the light source device 30. A doctor operates the operation part to be able to curve the insertion part in an arbitrary direction. By doing this, the inside of the hollow organ can be freely observed by using an image captured by an imaging element 11. Note that the imaging element 11 is, for example, a charge coupled device (CCD) image sensor, a complementary MOS (CMOS) image sensor, or the like, and is an example of an imaging sensor of the medical system 1. It is sufficient if the imaging element 11 is provided in the endoscope. The imaging element 11 may be provided, for example, at a distal end of the insertion part, or may be provided on a base end side of the insertion part, that is, near the operation part.

The insertion part of the endoscope 10 is further provided with a magnetic sensor 12, and a signal line from the magnetic sensor 12 is connected to the examination assistance device 40. The magnetic sensor 12 is disposed near the distal end of the insertion part. The magnetic sensor 12 detects a magnetic field generated by the magnetic field generation device 60 to detect a position and an orientation of the distal end of the insertion part, that is, spatial disposition of the distal end of the insertion part. The magnetic sensor 12 is, for example, a six-axial sensor that includes two cylindrical coils for which central axes are orthogonal to each other. The magnetic sensor 12 detects position coordinates and a Euler angle of the distal end of the insertion part, and outputs the position coordinates and the Euler angle to the examination assistance device 40.

Note that FIGS. 1 and 2 illustrate an example where the magnetic field generation device 60 generates a predetermined magnetic field, and the magnetic sensor 12 provided in the endoscope 10 detects the magnetic field generated by the magnetic field generation device 60. However, a magnetic field generation device may be provided in the endoscope 10, and a magnetic sensor that is disposed in a predetermined position may detect a magnetic field generated from the endoscope 10 to detect spatial disposition of the distal end of the insertion part of the endoscope 10.

The image processing device 20 is a video processor that processes an image captured by the endoscope 10. The image processing device 20 converts, for example, a signal from the endoscope 10 into a video signal, and outputs the video signal to the display device 50. By doing this, the display device 50 displays a live image on the basis of the video signal from the image processing device 20. In addition, the image processing device 20 may control the light source device 30, for example, on the basis of the video signal, and may perform processing relating to automatic dimming control. Further, the image processing device 20 is also connected to the examination assistance device 40, and outputs an image processed by the image processing device 20 to the examination assistance device 40.

The light source device 30 is a device that supplies illumination light to the endoscope 10 through a light guide. Illumination light supplied by the light source device 30 is not particularly limited, but may be, for example, white light to be used in normal light observation of an endoscope, or may be special light to be used in special light observation such as narrow band imaging (NBI) observation or autofluorescence imaging (AFI) observation. In addition, the light source device 30 may arbitrarily switch, for example, white light and special light according to selection of a doctor, and may supply white light or special light to the endoscope 10.

The examination assistance device 40 is a device that processes, in real time, information that has been obtained during endoscopy to generate auxiliary information. The examination assistance device 40 is a device that generates an examination plan on the basis of a result of endoscopy. Note that the auxiliary information includes an organ model, polyp information, current position information, or the like that will be described below.

The examination assistance device 40 may be a general-purpose computer such as a personal computer, a tablet, or another mobile device, or may be an application-specific computer, a workstation, or a mainframe computer. In addition, the examination assistance device 40 may be a single device, may be a set of a plurality of devices, or may be configured as a distributed computing system. The examination assistance device 40 is configured to execute a variety of software programs including a software program for performing all or some of the processes and algorithms disclosed herein. The examination assistance device 40 serving as an example includes a processor 41 that is configured to process an image that has been received as an input for various algorithms and software programs, and non-image information such as spatial disposition information, as illustrated in FIG. 2.

The processor 41 may include hardware, and the hardware may include, for example, at least one of a circuit that processes a digital signal and a circuit that processes an analog signal. The processor 41 can include, for example, one or a plurality of circuit devices (for example, ICs) or one or a plurality of circuit elements (for example, resistors or capacitors) on a circuit board. The processor 41 may be a central processing unit (CPU). In addition, as the processor 41, various types of processors including a graphics processing unit (GPU) and a digital signal processor (DSP) may be used. The processor 41 may be a hardware circuit including an application specific integrated circuit (ASIC) or a field-programmable gate array (FPGA). The processor 41 can include an amplifier circuit, a filter circuit, or the like that processes an analog signal.

The examination assistance device 40 serving as an example includes a storage device 42, as illustrated in FIG. 2. A software program and/or a computer-executable command to be executed by the processor 41 are stored in a computer-readable storage medium such as the storage device 42. Note that a "computer-readable storage medium" used herein refers to a non-transitory computer-readable storage medium.

The examination assistance device 40 can include one or a plurality of storage devices 42. The storage device 42 can include a memory and/or another storage device. The memory may be, for example, a random access memory (RAM) of a computer. The memory may be a semiconductor memory such as a static random access memory (SRAM) or a dynamic random access memory (DRAM). The storage device 42 may be, for example, a register, a magnetic storage device such as a hard disk device, an optical storage device such as an optical disk device, an internal or external hard disk drive, a server, a solid state storage device, a CD-ROM, a DVD, another optical or magnetic disk storage device, or another storage device.

The computer-executable command includes, for example, a command and data that cause the examination assistance device 40 to achieve a fixed function or a group of functions. These computer-executable commands are executed by the processor 41, and therefore the processor 41 exhibits predetermined functions. The computer-executable command may be a set of commands that configures a software program, or may be a command that is directly processed by the hardware circuit of the processor 41.

The examination assistance device 40 serving as an example further includes a display interface 43, an image fetching device 44, a spatial disposition detection device 45, a driving circuit 46, and an input interface 47, as illustrated in FIG. 2.

The display interface 43 outputs, to the display device 50, auxiliary information that has been generated by the processor 41 on the basis of an image fetched from the image fetching device 44 and spatial disposition information generated by the spatial disposition detection device 45. By doing this, the display device 50 displays the auxiliary information together with a live image.

The image fetching device 44 is a device that fetches, in every fixed period, an endoscopic image that has been captured by the endoscope 10 and on which the image processing device 20 has performed predetermined processing. The image fetching device 44 may obtain, from the image processing device 20, for example, 30 endoscopic images per second in the same manner as a frame rate. In addition, in contrast to the frame rate, for example, three endoscopic images per second may be obtained by using a long period in comparison with the frame rate.

The spatial disposition detection device 45 controls the driving circuit 46 that drives the magnetic field generation device 60, and causes the magnetic field generation device 60 to generate a predetermined magnetic field. The spatial disposition detection device 45 detects the magnetic field by using the magnetic sensor 12, and generates, in real time, data relating to position coordinates (x, y, z) and an orientation (a Euler angle ($\psi$, $\theta$, $\varphi$)), that is, spatial disposition information, of the distal end of the insertion part on the basis of a detection signal of the detected magnetic field.

The input interface 47 is connected to the input device 70 such as a keyboard, a mouse, a touch panel, a sound input device, or a foot pedal. An operation signal that corresponds to an operation performed on the input device 70 is input to the processor 41 through the input interface 47.

Figure 3:
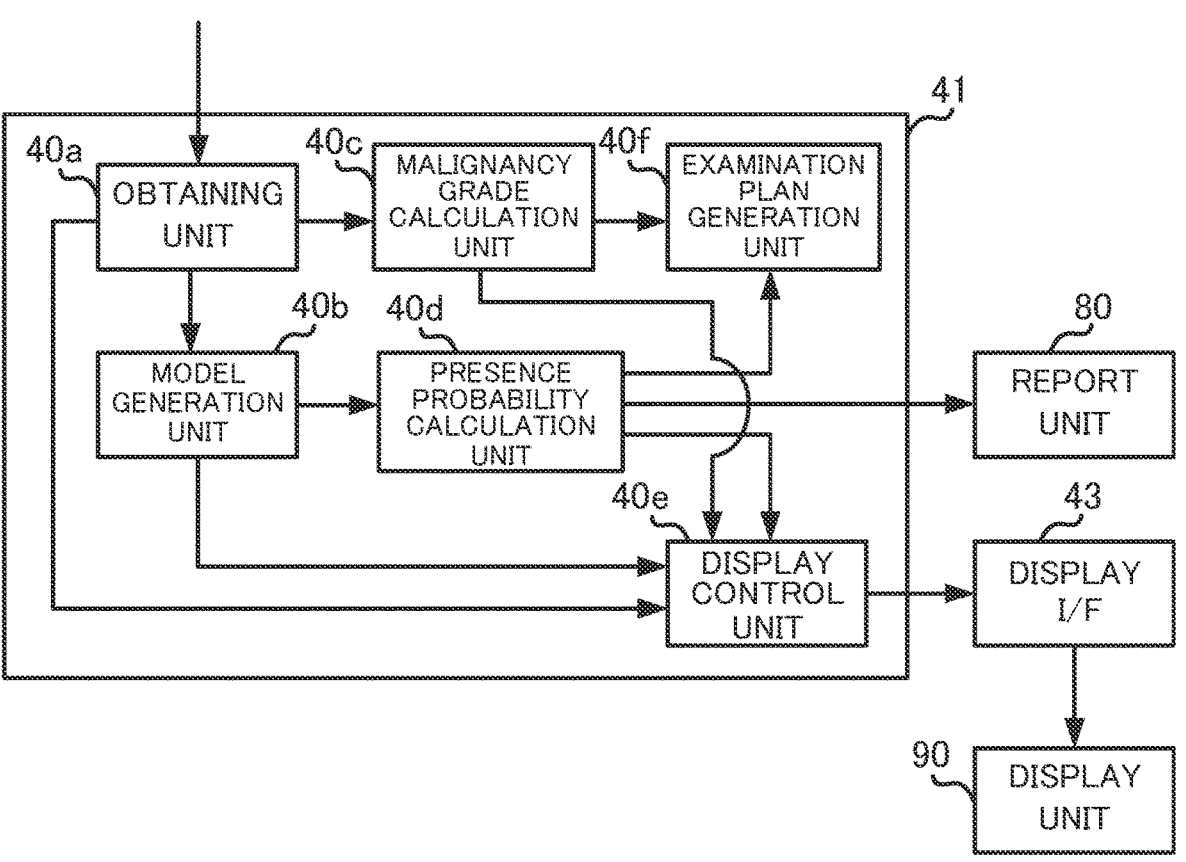
FIG. 3 is a block diagram illustrating a functional configuration of a processor according to an embodiment.
Figure 4:
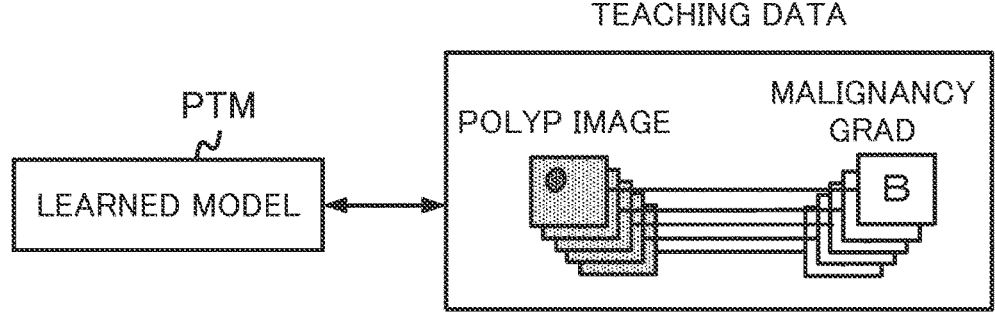
FIG. 4 is a diagram for explaining a learned model.
Figure 5:
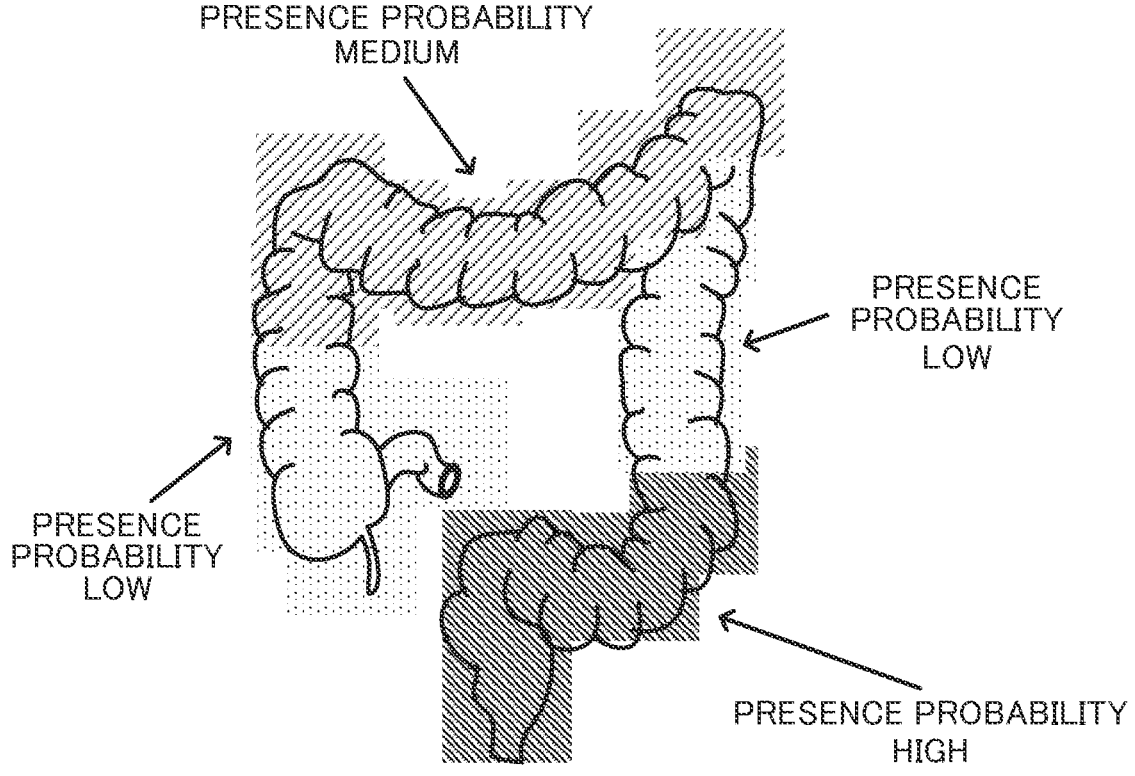
FIG. 5 is a diagram illustrating a relationship between a position inside a hollow organ and a polyp presence probability.

FIG. 3 is a block diagram illustrating a functional configuration of a processor according to an embodiment. FIG. 4 is a diagram for explaining a learned model. FIG. 5 is a diagram illustrating a relationship between a position inside a hollow organ and a polyp presence probability. In the examination assistance device 40 described above, the processor 41 executes a software program, and therefore the processor 41 achieves the functions illustrated in FIG. 3. Functions of the processor 41 are described below with reference to FIGS. 3 to 5.

The processor 41 includes an obtaining unit 40a, a model generation unit 40b, a malignancy grade calculation unit 40c, a presence probability calculation unit 40d, a display control unit 40e, and an examination plan generation unit 40f, as illustrated in FIG. 3.

The obtaining unit 40a obtains an endoscopic image that has been captured by the imaging element 11 in a hollow organ of a patient, and spatial disposition information of the distal end of the insertion part. Specifically, the obtaining unit 40a obtains an endoscopic image from the image processing device 20 by using the image fetching device 44, and obtains spatial disposition information that has been generated by the spatial disposition detection device 45.

The model generation unit 40b generates an organ model indicating a stereoscopic structure of a hollow organ of a patient Pa, on the basis of the endoscopic image and the spatial disposition information that have been obtained by the obtaining unit 40a. In this example, the hollow organ is the large intestine, and the organ model is a large intestine model. Specifically, the model generation unit 40b may generate the organ model, for example, on the basis of an endoscopic image obtained in every fixed period and spatial disposition information at the time of obtaining each of the endoscopic images by using visual simultaneous localization and mapping (SLAM). Visual SLAM is a technology for simultaneously estimating pieces of three-dimensional information of a plurality of feature points, and a position and an orientation of a camera on the basis of an image captured by the camera. In the medical system 1, the position and the orientation of the camera correspond to a position and an orientation of the distal end of the insertion part. Therefore, processing can be performed in a state where the position and the orientation of the camera are known due to spatial disposition information, and this enables three-dimensional information to be calculated at high speed and with high precision.

The malignancy grade calculation unit 40c calculates a malignancy grade of a polyp that is present in an observed region inside the hollow organ, on the basis of the endoscopic image obtained by the obtaining unit 40a. Note that the observed region refers to a region that has been imaged by the imaging element 11 inside the hollow organ. Specifically, the malignancy grade calculation unit 40c analyzes an endoscopic image to detect a polyp, and calculates a malignancy grade of the detected polyp. More specifically, the malignancy grade calculation unit 40c may estimate a position of a polyp in an endoscopic image and a malignancy grade of the polyp, for example, by using a learned model PTM obtained by learning a malignancy grade of a polyp specified from a polyp image in association with a surface shape of the polyp, as illustrated in FIG. 4. Note that the learned model PTM may be generated in advance for each race, age, gender, life style (the presence/absence of a smoking habit, the presence/absence of a drinking habit, or the like), medical history, or the like of a patient, and the malignancy grade calculation unit 40c may appropriately select a learned model to be used, on the basis of patient information of the patient Pa. Note that the patient information includes race, age, gender, life style (the presence/absence of a smoking habit, the presence/absence of a drinking habit, or the like), medical history, or the like.

The presence probability calculation unit 40d calculates a polyp presence probability in a not-yet-observed region inside the hollow organ. The polyp presence probability may be a probability of presence of a polyp regardless of a malignancy grade of the polyp, or may be weighted according to the malignancy grade of the polyp. Note that the not-yet-observed region refers to a region that has not been imaged by the imaging element 11 inside the hollow organ. Specifically, the presence probability calculation unit 40d may specify a not-yet-observed region on the basis of at least the endoscopic image and the spatial disposition information that have been obtained by the obtaining unit 40a, and may calculate a polyp presence probability in the not-yet-observed region on the basis of a position of the not-yet-observed region that has been specified inside the hollow organ. More specifically, the presence probability calculation unit 40d may estimate the entire three-dimensional shape of the hollow organ of the patient Pa, for example, on the basis of the history of the spatial disposition information (that is, a locus of movement of the distal end of the insertion part of the endoscopic inside the lumen), and may specify the not-yet-observed region on the basis of the estimated entire shape and the organ model. Then, a polyp presence probability in the not-yet-observed region may be estimated, for example, by using information indicating a relationship between a position inside the hollow organ and the polyp presence probability, as illustrated in FIG. 5. Note that FIG. 5 illustrates an example where the rectum and the sigmoid colon have a highest polyp presence probability, and the descending colon and the cecum have a lowest polyp presence probability.

The display control unit 40e causes a display unit 90 to display at least the organ model and non-observation information that specifies a position of the not-yet-observed region on the organ model. In addition, the display control unit 40e causes the display unit 90 to display polyp information that specifies a position and a malignancy grade of a polyp inside the hollow organ on the organ model, in addition to the organ model and the non-observation information. Note that the display unit 90 is, for example, the display device 50. Specifically, the display control unit 40e may cause a position of a polyp to be indicated by displaying a predetermined mark on the organ model, and in this case, a malignancy grade of the polyp may be specified by using a size and color of the predetermined mark. In addition, the display control unit 40e may cause the display unit 90 to display current position information that specifies a current position of the distal end of the insertion part on the organ model, in addition to the organ model, the polyp information, and the non-observation information. The display control unit 40e also causes these pieces of auxiliary information (the organ model, the polyp information, the non-observation information, or the like) to be displayed, for example, in such a way that these pieces of auxiliary information are arranged next to a live image. Note that the auxiliary information may be displayed in such a way that the auxiliary information and the live image are switched according to an operation of a doctor.

The non-observation information is displayed on the organ model by the display control unit 40e, but a report unit 80 may report the presence of a not-yet-observed region in order to attract attention of a doctor who is conducting an examination. Specifically, for example, the malignancy grade calculation unit 40c may cause the report unit 80 to report the presence of a not-yet-observed region by using sound, light, or the like, in a case where a polyp presence probability in the not-yet-observed region is greater than or equal to a predetermined threshold. By doing this, the doctor reliably recognizes the presence of a not-yet-observed region that particular attention needs to be paid to, and this can prevent the doctor from unintentionally omitting an examination.

The examination plan generation unit 40f generates an examination plan on the basis of at least the polyp presence probability that has been calculated by the presence probability calculation unit 40d. The examination plan includes a schedule of the next examination of the hollow organ. This schedule may be, for example, recommended examination date, a recommended period before the next examination, or the like, or may be determined examination date and time. In addition, the examination plan generation unit 40f may generate the examination plan on the basis of at least a polyp malignancy grade of a polyp that has been calculated by the malignancy grade calculation unit 40c and the polyp presence probability that has been calculated by the presence probability calculation unit 40d. In this case, the examination plan may include a schedule of treatment/surgery for removing the polyp during examination. Specifically, the examination plan generation unit 40f may set a schedule for conducting a reexamination earlier, for example, as a detected polyp has a higher malignancy grade or there is a higher polyp presence probability in a not-yet-observed region.

The report unit 80 may be, for example, a speaker that attracts attention of an operator by using sound, a lamp or light that attracts attention of the operator by using light, a vibrator that attracts attention of the operator by using vibration, or the like. Note that the display unit 90 described below may also serve as the report unit 80.

The display device 50 serving as an example of the display unit 90 is, for example, a liquid crystal display, a plasma display, an organic EL display, a CRT display, an LED matrix panel, electronic paper, a projector, or the like, and may be a display device of another type. In addition, the display device 50 may stereoscopically display an image. A scheme for displaying an 3D image of the display device 50 is not particularly limited, and an arbitrary display scheme can be employed. For example, a naked-eye scheme may be employed, or a scheme for displaying a stereoscopic image in combination with glasses or the like that an operator wears may be employed.

By employing the medical system 1 configured as described above, a next examination schedule is automatically generated on the basis of information obtained during examination. By doing this, a specific examination schedule is reliably provided to a patient, and this enables the patient to strongly recognize the necessity of examination. In addition, an examination schedule is generated in consideration of a possibility of presence of a polyp in a not-yet-observed region. By doing this, even in a case where there is a region that has failed to be observed or a region that has not been observed in current endoscopy under some restrictions, reexamination at an appropriate timing is proposed according to the necessity of examination of the region. Therefore, early treatment can be performed without overlooking a lesion. Further, in a case where an examination schedule is generated in consideration of a malignancy grade of a polyp that has been detected in endoscopy, a schedule that corresponds to the necessity of examination or treatment at a current point in time is set. This can avoid a situation where a lesion will be left as it is for a long time.

Figure 6:
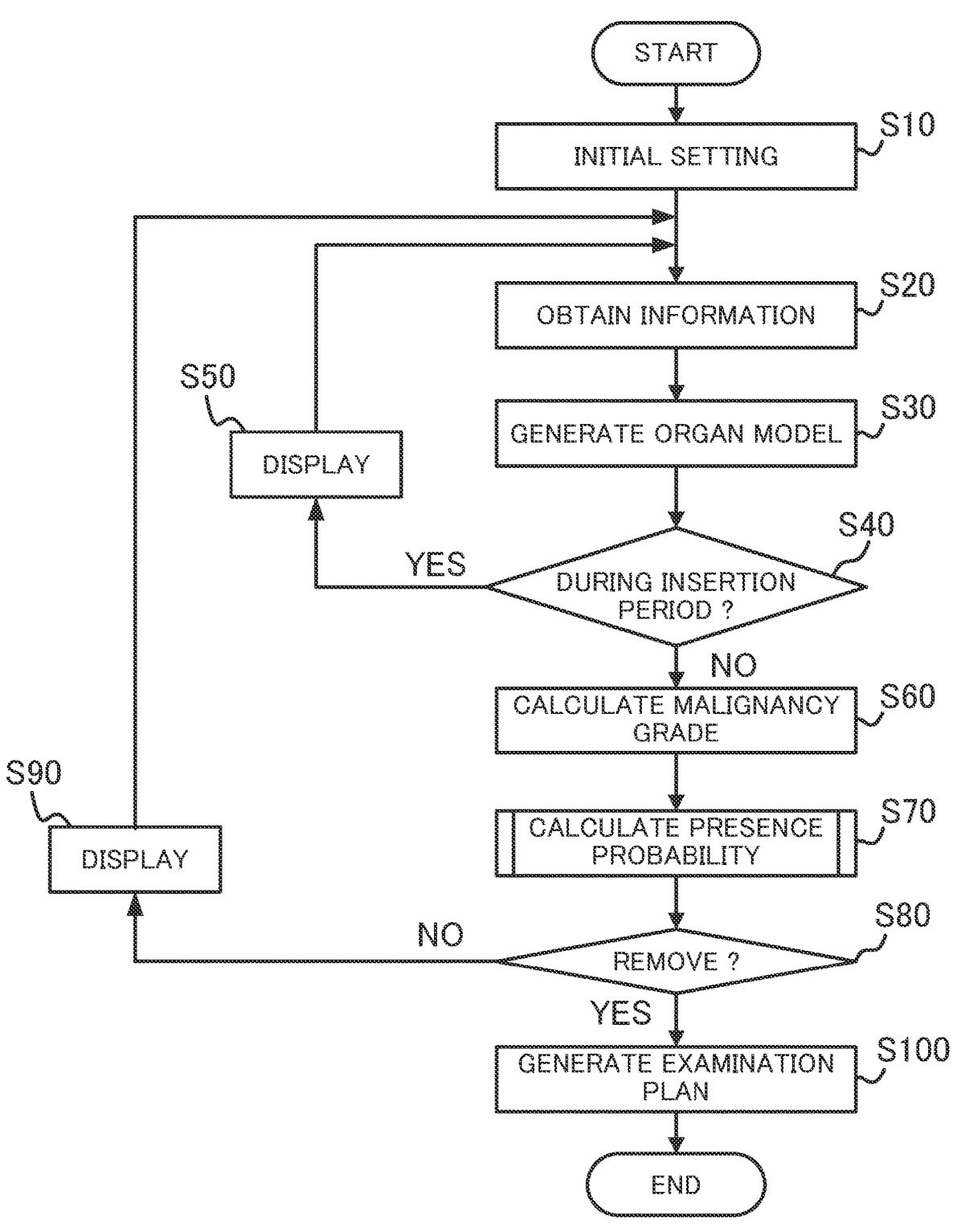
FIG. 6 is a flowchart of processing performed by a medical system according to an embodiment.
Figure 7:
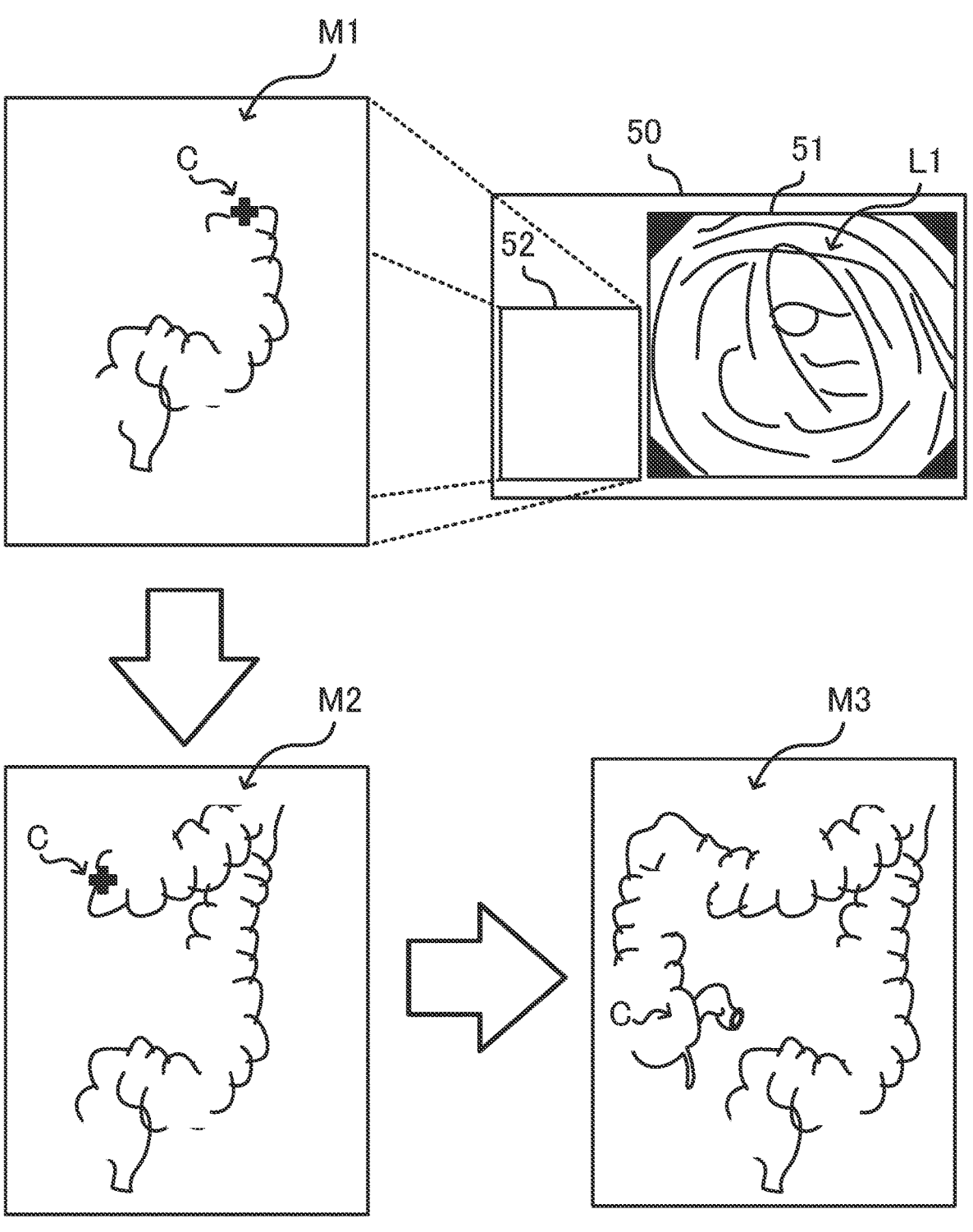
FIG. 7 is a diagram illustrating a display example of a model display region.
Figure 8:
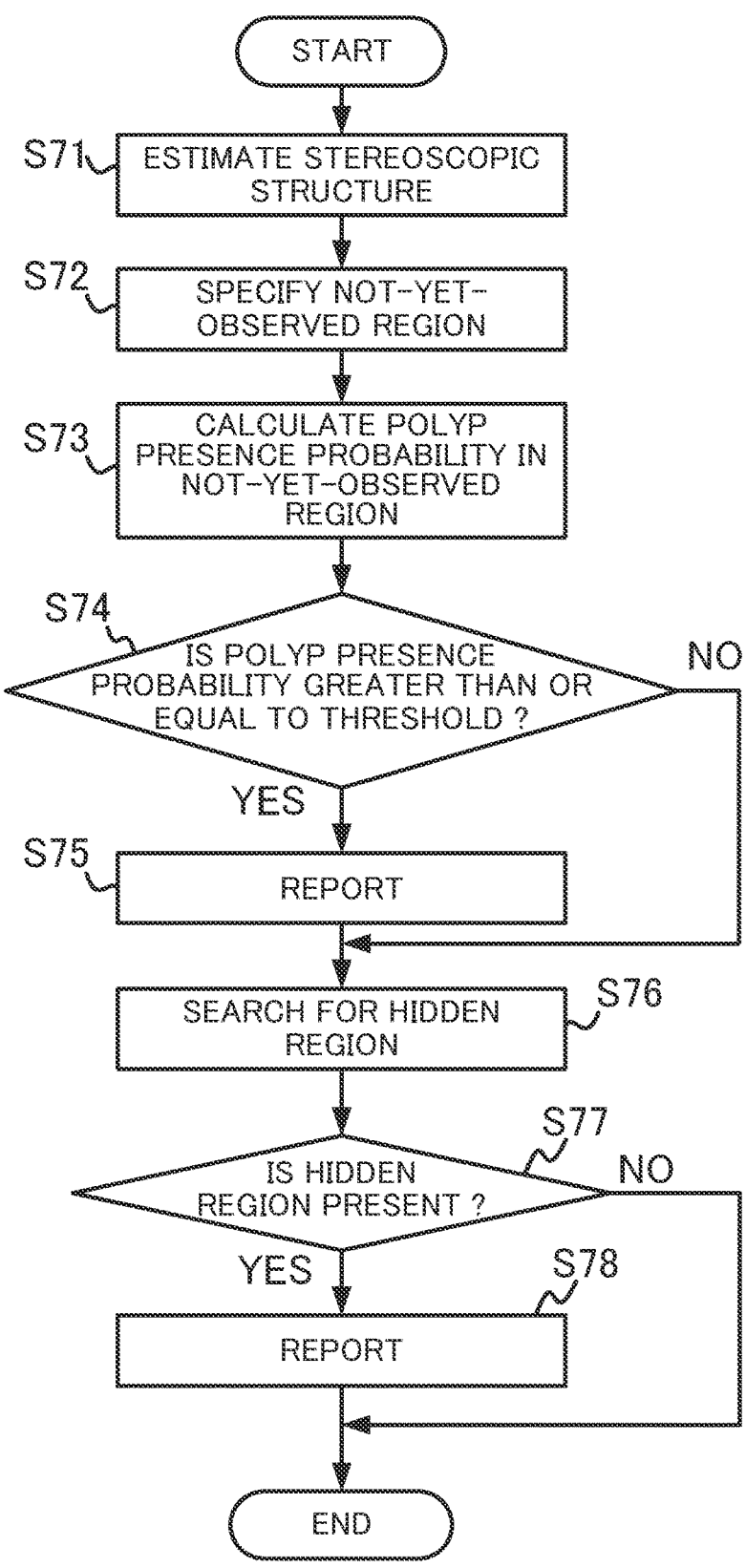
FIG. 8 is a flowchart of presence probability calculation processing performed by an examination assistance device.
Figure 9:
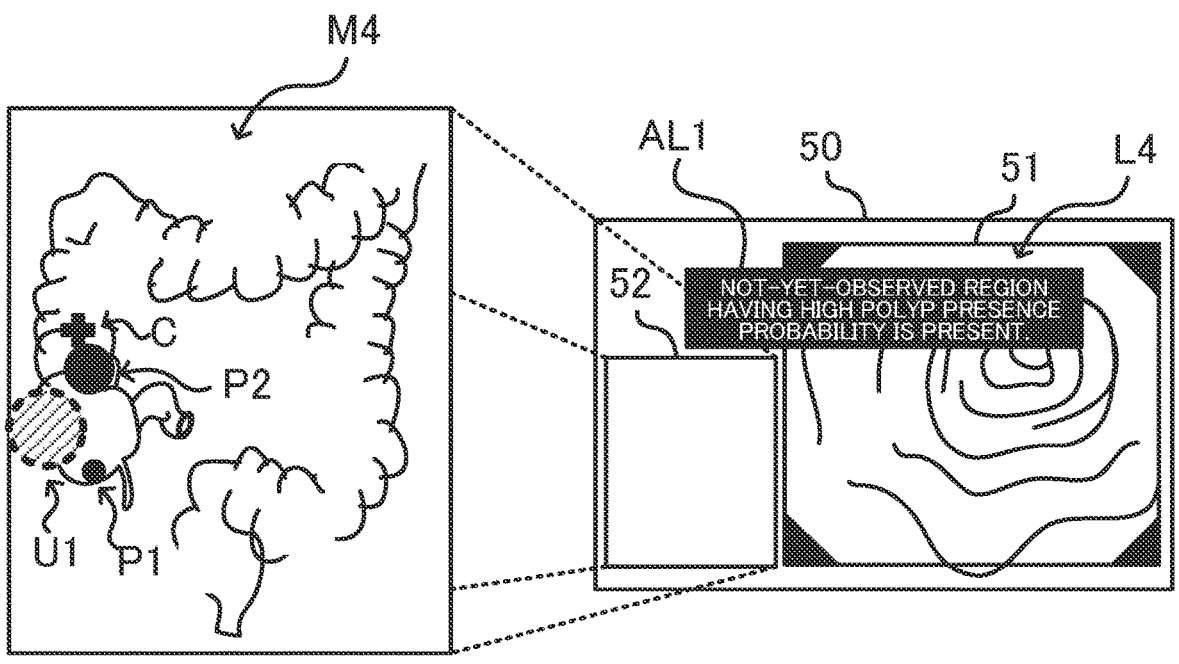
FIG. 9 is a diagram illustrating another display example of the model display region.
Figure 10:
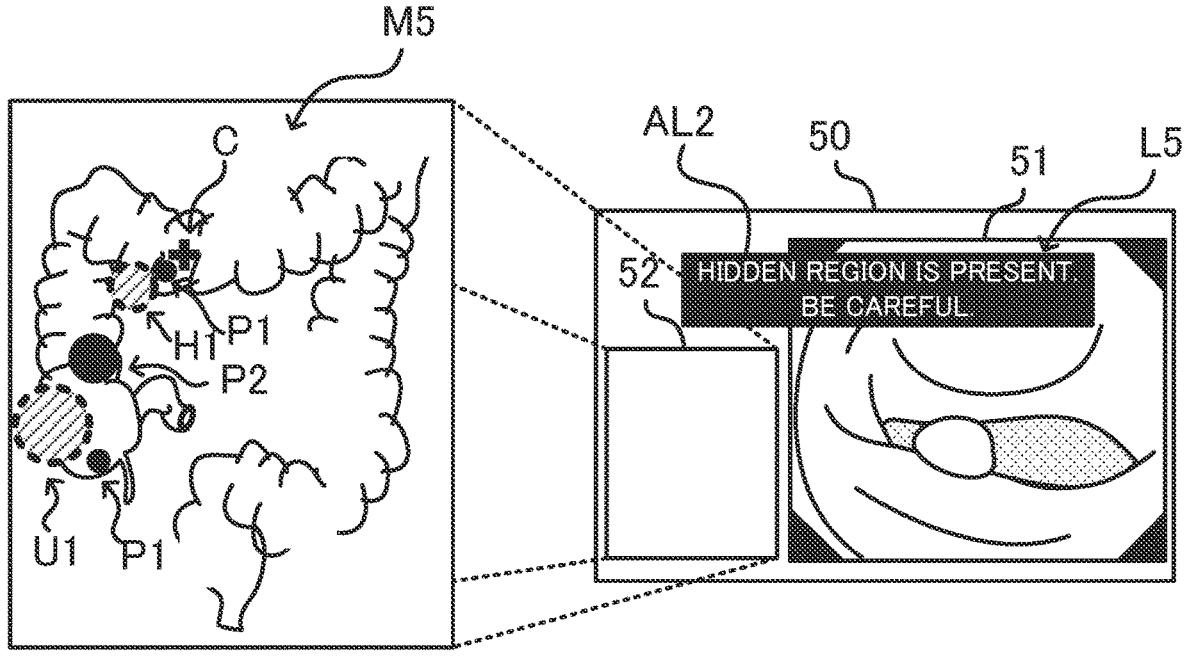
FIG. 10 is a diagram illustrating yet another display example of the model display region.
Figure 13:
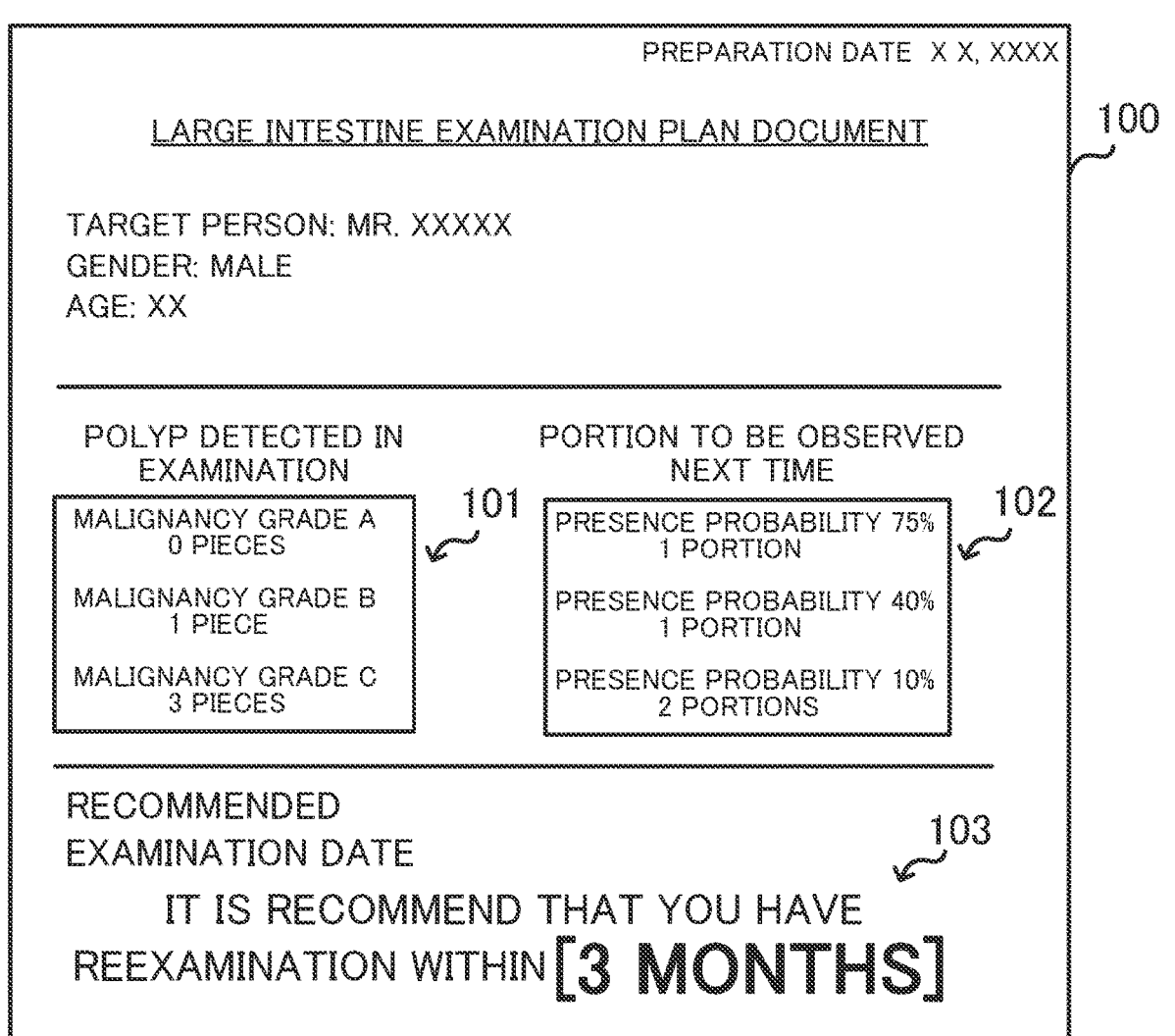
FIG. 13 is a diagram illustrating an examination plan document prepared by the medical system.

FIG. 6 is a flowchart of processing performed by a medical system according to an embodiment. FIG. 7 is a diagram illustrating a display example of a model display region. FIG. 8 is a flowchart of presence probability calculation processing performed by an examination assistance device. FIG. 9 is a diagram illustrating another display example of the model display region. FIG. 10 is a diagram illustrating yet another display example of the model display region. FIG. 11 is a diagram for explaining an example of a method for determining recommended examination date. FIG. 12 is a diagram for explaining another example of the method for determining recommended examination date. FIG. 13 is a diagram illustrating an examination plan document prepared by the medical system. An information processing method performed by the medical system 1 for assisting endoscopy is described in detail below with reference to FIGS. 6 to 13.

When examination has been started, first, the medical system 1 receives an input of initial settings (step S10). Here, the examination assistance device 40 sets various types of information required in processing that follows. Specifically, the processor 41 of the examination assistance device 40 extracts information relating to the patient Pa from a predetermined database according to an input of a doctor, and sets the information as basic information. The basic information includes, for example, name, race, age, gender, life style (the presence/absence of a smoking habit, the presence/absence of a drinking habit, or the like), medical history, or the like of the patient Pa. Information relating to colonoscopy or another examination in the past, or the like may also be included. Further, the processor 41 detects an operation performed on the endoscope 10 by the doctor to set a reference position and a reference orientation. For example, the doctor performs a predetermined operation in a state where the doctor has aligned the distal end of the endoscope 10 with the anus of the patient Pa who is lying on a bed 2, and therefore the processor 41 registers a position and an orientation that have been detected as a reference position and a reference orientation. By doing this, spatial disposition information to be generated later by the examination assistance device 40 is generated as information relating to spatial disposition on a three-dimensional orthogonal coordinate system that has been defined by the reference position and the reference orientation.

When initial setting has been completed, the doctor starts inserting the endoscope 10 into the large intestine, advances the endoscope 10 in the order of the anus, the rectum, the colon, and the cecum, and makes the endoscope 10 reach the deepest part of the large intestine. A period during which the endoscope 10 is inserted from the anus to the deepest part of the large intestine, as described above, is referred to as an insertion period, and is distinguished from a pulling-out period that follows. Note that an examination period includes the insertion period and the pulling-out period. The pulling-out period is a period during which the endoscope 10 is pulled out from the deepest part toward the anus, and the doctor observes the inside of the large intestine during the pulling-out period, and performs treatment such as removal of a polyp.

During the examination period, the medical system 1 obtains an endoscopic image and spatial disposition information (step S20), and generates an organ model on the basis of the obtained information (step S30). Then, if it is during the insertion period (YES in step S40), the medical system 1 displays auxiliary information including the organ model, together with a live image (step S50). An operation during the insertion period is described in more detail below.

In step S20, the image processing device 20 performs predetermined image processing on an endoscopic image captured by the endoscope 10, and outputs the endoscopic image to the examination assistance device 40. Then, the processor 41 of the examination assistance device 40 obtains the endoscopic image that has been fetched by the image fetching device 44 from the image processing device 20, for example, at 30 fps. Further, the processor 41 obtains spatial disposition information that has been generated by the spatial disposition detection device 45 on the basis of a result of detection performed by the magnetic sensor 12, in synchronization with the fetching of the endoscopic image. As described above, the medical system 1 periodically obtains an endoscopic image, and spatial disposition information that corresponds to the endoscopic image.

In step S30, the processor 41 of the examination assistance device 40 generates a large intestine model of the patient Pa by using the endoscopic image and the spatial disposition information that have been obtained in step S20. In the examination assistance device 40, the processor 41 extracts a plurality of feature points from consecutive endoscopic images that have been obtained at 30 fps, and calculates pieces of coordinate information of the plurality of feature points by using a technique such as visual SLAM. Then, these pieces of coordinate information of the plurality of feature points are used to generate a large intestine model indicating a three-dimensional structure of the large intestine of the patient Pa. Note that by using spatial disposition information that has been obtained by using the magnetic sensor 12 and indicates a position and an orientation of the distal end of the insertion part, the processor 41 can calculate coordinate information of a feature point at high speed and with high precision in comparison with a case where the coordinate information of the feature point is only calculated on the basis of image information.

In step S50, the processor 41 of the examination assistance device 40 causes the display device 50 to display auxiliary information including the organ model by using the display interface 43. Specifically, the processor 41 causes the display device 50 to display an organ model Ml that has been generated in step S30 on a model display region 52 adjacent to a live image display region 51 that displays a live image L1, as illustrated in FIG. 7.

Note that part of the organ model displayed on the display device 50 is missing, because the organ model is generated by using a set of feature points that have been extracted from endoscopic images. Stated another way, an organ model is not generated for a region for which an endoscopic image has not been captured. For example, in the organ model M1, part of the rectum, part of the sigmoid colon, and the like are missing. This indicates that corresponding regions have not been imaged during the insertion period. In addition, current position information C displayed on the organ model M1 is information that specifies a current position of the distal end of the insertion part on the organ model M1. The current position information C is generated on the basis of latest spatial disposition information.

The processes of step S20 to step S50 are repeatedly performed during the insertion period, and therefore auxiliary information to be displayed on the display device 50 together with the live image is updated at all times. FIG. 7 illustrates a state where the auxiliary information is updated during the insertion period. The organ model M1 is an organ model that has been generated at the time of insertion of the endoscope 10 up to the middle of the descending colon. An organ model M2 is an organ model that has been generated at the time of insertion of the endoscope 10 up to the middle of the transverse colon. An organ model M3 is an organ model that has been generated at the time of insertion of the endoscope 10 up to the cecum.

When the insertion period has finished (NO in step S40), the medical system 1 performs malignancy grade calculation processing for calculating a malignancy grade of a polyp that has been detected from the endoscopic images, and the presence probability calculation processing illustrated in FIG. 8 (step S60 and step S70). Stated another way, the malignancy grade calculation processing and the presence probability calculation processing are performed during the pulling-out period. Note that whether the insertion period has finished may be determined on the basis of a locus of movement of the distal end of the insertion part that has been calculated from the history of spatial disposition information. For example, the processor 41 of the examination assistance device 40 may determine that the insertion period has finished in a case where it has been detected that the distal end of the insertion part is turning back through a route that the distal end of the insertion part has previously passed through.

In step S60, the processor 41 of the examination assistance device 40 selects a learned model on the basis of the basic information that has been set in step S10, and inputs an endoscopic image to the selected learned model. Then, the processor 41 uses the learned model to detect a position of a polyp in a case where the polyp is present in the endoscopic image, and classifies the endoscopic image according to a malignancy grade of the detected polyp.

In the presence probability calculation processing of step S70, the medical system 1 first estimates a stereoscopic structure of the large intestine of the patient Pa (step S71). Here, the processor 41 of the examination assistance device 40 estimates the stereoscopic structure of the large intestine of the patient Pa on the basis of at least the spatial disposition information that has been obtained during the insertion period. Specifically, for example, a locus of movement of the distal end of the insertion part may be calculated from the history of the spatial disposition information that has been obtained during the insertion period, and the calculated locus of movement may be compared with a general shape of the large intestine that has been determined on the basis of the basic information of the patient Pa (age, gender, race, or the like of the patient Pa), and therefore a stereoscopic structure of the large intestine of the patient Pa on a three-dimensional orthogonal coordinate system that defines the spatial disposition information may be estimated.

When the stereoscopic structure of the large intestine has been estimated, the medical system 1 then specifies a not-yet-observed region (step S72). Here, the processor 41 of the examination assistance device 40 specifies the not-yet-observed region on the basis of at least the stereoscopic structure estimated in step S71 and the organ model generated in step S30. Specifically, for example, the processor 41 may exclude a region for which an organ model has been generated from the estimated stereoscopic structure, and may specify a remaining region as the not-yet-observed region. In addition, in order to avoid a situation where a region that has a possibility of observation during the pulling-out period is specified as the not-yet-observed region, the processor 41 may specify the not-yet-observed region on the basis of current position information of the distal end of the insertion part during the pulling-out period in addition to the estimated stereoscopic structure and the organ model. Specifically, the not-yet-observed region may be specified in a region on an upstream side of the large intestine (a side of the cecum) of a current position.

When the not-yet-observed region has been specified, the medical system 1 calculates a polyp presence probability in the specified not-yet-observed region (step S73). Here, the processor 41 of the examination assistance device 40 may calculate the polyp presence probability in the not-yet-observed region on the basis of a known relationship between a position in the large intestine and the polyp presence probability, as illustrated in FIG. 5.

If the polyp presence probability is greater than or equal to a threshold (YES in step S74), the medical system 1 reports the presence of the not-yet-observed region (step S75). Here, the processor 41 of the examination assistance device 40 may report, to the doctor, the presence of a not-yet-observed region having a high polyp presence probability, for example, by causing the display device 50 to display an alert AL1 on a live image L4 that the doctor is paying attention to, as illustrated in FIG. 9. In addition, the processor 41 may report, to the doctor, the presence of a not-yet-observed region having a high polyp presence probability by causing peripheral equipment serving as the report unit 80 to raise an alert by using sound, light, vibration, or the like.

Further, the medical system 1 searches for a hidden region (step S76). The hidden region refers to a region that fails to be checked on an endoscopic image and serves as a blind spot, such as a rear side of folds called haustra coli of the large intestine. The hidden region that is a blind spot in an endoscopic image is a region that illumination light is not applied to and is darker than another region, and brightness gradually reduces in a region between a region in a field of view of the imaging element 11 and the hidden region. Stated another way, a difference in luminance between pixels changes near the hidden region. By using this point, the processor 41 may detect the presence of the hidden region in the field of view of the imaging element 11 on the basis of a distribution of luminance in an endoscopic image.

Note that a region that is a blind spot in a current field of view but has already been imaged may fail to be detected as the hidden region. Therefore, the processor 41 may detect, as the hidden region, a region that has a large difference in luminance and for which a large intestine model has not been generated.

When the hidden region has been detected (YES in step S77), the medical system 1 reports the presence of the hidden region that has been detected (step S78). Here, the processor 41 of the examination assistance device 40 may report the presence of the hidden region to the doctor, for example, by causing the display device 50 to display an alert AL2 on a live image L5 that the doctor is paying attention to, as illustrated in FIG. 10. In addition, the processor 41 may report the presence of the hidden region to the doctor by causing peripheral equipment serving as the report unit 80 to raise an alert by using sound, light, vibration, or the like.

Note that this example indicates an example where a report is issued when the presence of the hidden region has been detected. However, when the hidden region has been detected, a polyp presence probability in the hidden region may be calculated, and a report may only be issued in a case where the polyp presence probability is greater than or equal to a threshold. It is sufficient if the polyp presence probability in the hidden region is calculated on the basis of a known relationship between a position of the hidden region in the large intestine and a polyp presence probability, similarly to a case where a polyp presence probability in the not-yet-observed region is calculated.

When the presence probability calculation processing has terminated, the medical system 1 determines whether the endoscope 10 has been removed from the large intestine. In a case where the endoscope 10 has not been removed (NO in step S80), auxiliary information including the organ model, polyp information, and non-observation information is displayed together with a live image (step S90).

In step S90, the processor 41 of the examination assistance device 40 causes the display device 50 to display auxiliary information including the polyp information and the non-observation information in addition to the organ model. Specifically, the processor 41 causes the display device 50 to display an organ model M4 that has been generated in step S30 on the model display region 52 adjacent to the live image display region 51, and display the polyp information that has been detected in step S60 and the non-observation information that has been detected in step S70 on the organ model M4, as illustrated in FIG. 9. It is sufficient if the polyp information is information that specifies a position and a malignancy grade of a polyp in the large intestine on the organ model M4, and the polyp information may be, for example, a predetermined mark (in this example, a black circle) that is displayed in the position of the polyp on the organ model M4 to have a size that corresponds to the malignancy grade of the polyp, as illustrated as polyp information P1 and polyp information P2 in FIG. 9. Note that the polyp information P1 indicates a position of a polyp having a low malignancy grade, and the polyp information P2 indicates a position of a polyp having a medium malignancy grade. In addition, it is sufficient if the non-observation information is information that specifies a position of the not-yet-observed region in the large intestine on the organ model M4, and the not-yet-observed information may be a mark that can be distinguished from the polyp information, as illustrated as not-yet-observed region information UI in FIG. 9. Note that the not-yet-observed region information may include information that specifies a polyp presence probability in the not-yet-observed region in addition to the information that specifies the position of the not-yet-observed region. In this case, the poly presence probability may be indicated, for example, by using color. Further, the processor 41 of the examination assistance device 40 may cause the display device 50 to display hidden region information H1 on an organ model M5 in one aspect of the non-observation information, as illustrated in FIG. 10, and the processor 41 may also cause the display device 50 to display, on the organ model M5, a hidden region that has already been observed in an aspect that can be distinguished from the not-yet-observed region.

The processes of step S20 to step S90 are repeatedly performed during the pulling-out period, and therefore auxiliary information that is to be displayed on the display device 50 together with a live image and includes the polyp information and the non-observation information is updated at all times.

When the pulling-out period has finished and the endoscope 10 has been removed from the large intestine (YES in step S80), the medical system 1 generates an examination plan on the basis of information obtained during endoscopy (step S100). Here, the processor 41 of the examination assistance device 40 determines recommended examination date on the basis of at least the polyp presence probability calculated in step S70, and generates an examination plan including the recommended examination date.

Specifically, the processor 41 refers to, for example, a table T1 in which standards that doctors conventionally use to determine recommended examination date on the basis of a probability of presence of an unknown polyp (the polyp presence probability) have been recorded, as illustrated in FIG. 11, and determines recommended examination date on the basis of the polyp presence probability.

In addition, in step S100, the processor 41 may determine recommended examination date on the basis of at least the polyp presence probability calculated in step S70 and the malignancy grade of a polyp that has been calculated in step S60, and may generate an examination plan including the recommended examination date. In this case, for example, the processor 41 may refer to the table T1 illustrated in FIG. 11, and may provisionally determine first recommended examination date on the basis of the polyp presence probability. Further, the processor 41 may refer to a table T2 in which standards that doctors conventionally use to determine recommended examination date on the basis of a malignancy grade have been recorded, as illustrated in FIG. 12, and may provisionally determine second recommended examination date on the basis of the malignancy grade. Finally, for example, the processor 41 may compare the first recommended examination date with the second recommended examination date, and may determine earlier recommended date as recommended examination date.

The processor 41 of the examination assistance device 40 may output the examination plan generated in step S100 as an examination plan document 100 including recommended examination date information 103, as illustrated in FIG. 13, and may provide the examination plan document 100 to the patient Pa. In this case, the processor 41 may present presence probability information 102 that has been used to generate the recommended examination date information 103, as a basis of an examination schedule, in the examination plan document 100. Further, in a case where a malignancy grade of a polyp has also been used to determine the recommended examination date, malignancy grade information 101 in addition to the presence probability information 102 may be presented, as a basis of the examination schedule, in the examination plan document 100.

As described above, the medical system 1 performs the processing illustrated in FIG. 6, and therefore an examination plan is generated in consideration of a region that has failed to be observed or a region that has not been observed in current endoscopy. Thus, a lesion can be prevented from being overlooked, and treatment can be early performed. In addition, a position of a not-yet-observed region is displayed on an organ model during endoscopy. Thus, a region that a doctor has not been intentionally observed can be easily distinguished from an unintentional not-yet-observed region on the basis of position information. Moreover, during the pulling-out period, the not-yet-observed region is specified by using current position information, and therefore the not-yet observed region can be appropriately determined. Thus, the presence of the not-yet-observed region can be reported to a doctor as information having high certainty.

The embodiments described above give specific examples that make the embodiment easily understandable, and embodiments are not limited to these embodiments. A medical system, an information processing method, and a program can be variously modified or altered without departing from the scope of the claims.

The embodiment described above has given an example where a malignancy grade or a presence probability of a polyp is calculated in real time during endoscopy, and an examination plan is generated after the endoscopy has finished. However, if the examination plan is only generated, the malignancy grade or the presence probability of the polyp may be calculated after endoscopy has finished. For example, an endoscopic image and spatial position information that have been obtained during endoscopy may be temporarily recorded. Thereafter, these pieces of information may be read at the timing of generating an examination plan, the malignancy grade or the presence probability of the polyp may be calculated, and an examination plan may be generated on the basis of these pieces of information.

In addition, the embodiment described above has given an example where a database of a relationship between a position of a polyp and a presence probability is generated, as illustrated in FIG. 5, and a presence probability that corresponds to a position is extracted from the database, and therefore the presence probability is calculated. However, the presence probability may be calculated by using a learned model using machine learning, similarly to the calculation of the malignancy grade. In this case, information relating to a position where a colorectal polyp has been present may be collected in advance regardless of endoscopy (including, for example, a large intestine CT colonography examination and the like), and these pieces of position information and a statistical polyp presence probability in each position may be learned as teaching data in a model. The teaching date may be classified in advance according to basic information (for example, Japanese adult males or the like), and the learned model may be generated for each class.

In addition, the embodiment described above has given an example where an organ model indicating a stereoscopic structure of a hollow organ is generated by using three-dimensional coordinate information of a feature point that has been extracted from an endoscopic image. However, the organ model is not limited to a three-dimensional model. It is sufficient if the organ model indicates a stereoscopic structure in such a way that a doctor can correctly recognize a position of a not-yet-observed region in a certain degree, and the organ model may be, for example a two-dimensional model indicating a bird's eye view of the hollow organ.

Moreover, the embodiment described above has given an example where spatial disposition including a position and an orientation of a distal end of an insertion part of an endoscope is detected by using a magnetic sensor. However, a means for detecting spatial disposition of the distal end of the insertion part is not limited to the magnetic sensor. For example, spatial disposition of the imaging element 11 may be detected by using a sensor that detects a shape of the endoscope 10 and a sensor that detects an amount of insertion of the endoscope 10. The spatial disposition of the distal end of the insertion part may be estimated by measuring an amount of traction of an operation wire that has been inserted into the insertion part. In addition, the spatial disposition of the distal end of the insertion part may be estimated on the basis of the history of an operation performed on an operation part that pulls or relaxes the operation wire. Further, the spatial disposition of the distal end of the insertion part may be estimated by combining the amount of traction or the history of the operation with detection information of a gyro sensor provided at the distal end of the insertion part. Moreover, the spatial disposition of the distal end of the insertion part may be estimated on the basis of information that has been obtained from a device other than the endoscope 10, and the device other than the endoscope 10 may be, for example, medical image equipment or the like.

In addition, the embodiment described above has given an example where a polyp is detected from an endoscopic image that has been obtained during a pulling-out period. However, a polyp may be detected by using an endoscopic image that has been obtained during an insertion period in addition to the endoscopic image that has been obtained during the pulling-out period.

What is claimed is:

1. A medical system comprising:
   a processor comprising hardware, wherein the processor is configured to:
      obtain an image of a region of a hollow organ imaged by an endoscope and spatial disposition information of a distal end of an insertion part of the endoscope generated at a time corresponding to a time at which the image is imaged by the endoscope;
      generate at least a region of an organ model of the region of the hollow organ that has been imaged, based on the image of the region of the hollow organ and the spatial disposition information;
      specify a not-yet-observed region of the hollow organ that has not yet been imaged by the endoscope, based on the region of the organ model generated; and
      calculate a presence probability of a lesion in the not-yet-observed region, based on information indicating a relationship between a position inside the hollow organ and a polyp presence probability,
   wherein the information indicating the relationship between the position inside the hollow organ and the polyp presence probability includes information that divides the hollow organ into at least two or more regions, and assigns a polyp presence probability to each of the at least two or more regions.

2. The medical system according to claim 1, wherein the processor is configured to generate an examination plan on a basis of at least the presence probability of the lesion, the examination plan including a schedule of a next examination of the hollow organ.

3. The medical system according to claim 1, wherein the lesion includes a polyp.

4. The medical system according to claim 1, wherein the at least the region of the organ model indicates a stereoscopic structure of the hollow organ, and wherein the processor is configured to:
   estimate the stereoscopic structure of the region of the hollow organ imaged by the endoscope; and
   specify the not-yet-observed region of the hollow organ based on at least the stereoscopic structure of the region of the hollow organ imaged by the endoscope that has been estimated.

5. The medical system according to claim 4, wherein the spatial disposition information is obtained during an insertion period of the endoscope into the hollow organ, and wherein the processor is configured to specify the not-yet-observed region of the hollow organ that has not yet been imaged by the endoscope during a pulling-out period of the endoscope from the hollow organ.

6. The medical system according to claim 5, wherein the processor is configured to specify the not-yet-observed region of the hollow organ based on the stereoscopic structure of the region of the hollow organ imaged by the endoscope that has been estimated, the region of organ model, and current position information of the distal end of the insertion part of the endoscope during the pulling-out period.

7. The medical system according to claim 4, wherein the processor is configured to calculate the presence probability of the lesion in the not-yet-observed region based on a position of the not-yet-observed region inside the hollow organ.

8. The medical system according to claim 7, wherein the processor is configured to:
   determine whether the presence probability of the lesion in the not-yet-observed region is greater than or equal to a predetermined threshold; and
   in response to determining that the presence probability of the lesion in the not-yet-observed region is greater than or equal to the predetermined threshold, cause a report unit to report presence of the not-yet-observed region.

9. The medical system according to claim 4, wherein the endoscope comprises an imaging sensor, and wherein the processor is configured to detect presence of a hidden region in a field of view of the imaging sensor on a basis of a distribution of luminance in the image of the region of the hollow organ.

10. The medical system according to claim 9, wherein the processor is configured to calculate a presence probability of a lesion in the hidden region based on at least a position of the hidden region inside the hollow organ.

11. The medical system according to claim 10, wherein the processor is configured to:

determine whether the presence probability of the lesion in the hidden region is greater than or equal to a predetermined threshold; and in response to determining that the presence probability of the lesion in the hidden region is greater than or equal to the predetermined threshold, cause a report unit to report presence of the hidden region.

12. The medical system according to claim 4, wherein the lesion includes a polyp, and wherein the processor is configured to cause a display to display at least the organ model, polyp information for specifying a position and a malignancy grade of the polyp inside the hollow organ on the organ model, non-observation information for specifying a position of the not-yet-observed region on the organ model.

13. The medical system according to claim 12, wherein the processor is configured to cause the display to display current position information that specifies a current position of the distal end of the insertion part of the endoscope on the organ model.

14. The medical system according to claim 12, wherein the processor is configured to cause the display to display at least the organ model, the polyp information, and the non-observation information in a state where the at least the organ model, the polyp information, and the non-observation information are arranged together with a live image that has been captured by the endoscope, or are switched to the live image.

15. The medical system according to claim 1, further comprising:

the endoscope configured to capture an optical image of the region of the hollow organ and output a signal based on the optical image; and a sensor configured to detect a spatial disposition of the distal end of the insertion part and output a signal based on the spatial disposition detected, wherein the processor is configured to:

generate the image of the region of the hollow organ based on the signal based on the optical image; and generate the spatial disposition information based on the signal based on the spatial disposition detected.

16. The medical system according to claim 15, wherein: the endoscope is an endoscope for a large intestine; and the hollow organ includes a large intestine.

17. The medical system according to claim 1, wherein: the processor is configured to:

determine whether an insertion period has finished using the spatial disposition information of the distal end of the insertion part of the endoscope;

in response to determining that the insertion period has finished, calculate the presence probability; and control an output device to output the presence probability of the lesion in the not-yet-observed region calculated.

18. An information processing method performed by a computer, wherein the information processing method comprising:

obtaining an image of a region of a hollow organ imaged by an endoscope and spatial disposition information of a distal end of an insertion part of the endoscope generated at a time corresponding to a time at which the image is imaged by the endoscope;

generating at least a region of an organ model of the region of the hollow organ that has been imaged, based on the image of the region of the hollow organ and the spatial disposition information;

specifying a not-yet-observed region of the hollow organ that has not yet been imaged by the endoscope, based on the region of the organ model generated;

calculating a presence probability of a lesion in the not-yet-observed region, based on information indicating a relationship between a position inside the hollow organ and a polyp presence probability; and controlling an output device to output the presence probability of the lesion in the not-yet-observed region calculated, wherein the information indicating the relationship between the position inside the hollow organ and the polyp presence probability includes information that divides the hollow organ into at least two or more regions, and assigns a polyp presence probability to each of the at least two or more regions.

19. A non-transitory computer-readable medium that stores a program that causes a computer to perform a process comprising:

obtaining an image of a region of a hollow organ imaged by an endoscope and spatial disposition information of a distal end of an insertion part of the endoscope generated at a time corresponding to a time at which the image is imaged by the endoscope;

generating at least a region of an organ model of the region of the hollow organ that has been imaged, based on the image of the region of the hollow organ and the spatial disposition information;

specifying a not-yet-observed region of the hollow organ that has not yet been imaged by the endoscope, based on the region of the organ model generated;

calculating a presence probability of a lesion in the not-yet-observed region, based on information indicating a relationship between a position inside the hollow organ and a polyp presence probability; and controlling an output device to output the presence probability of the lesion in the not-yet-observed region calculated, wherein the information indicating the relationship between the position inside the hollow organ and the polyp presence probability includes information that divides the hollow organ into at least two or more regions, and assigns a polyp presence probability to each of the at least two or more regions.

* * * * *